United States Patent [19]

Schnepp-Pesch et al.

[11] Patent Number: 5,540,713
[45] Date of Patent: Jul. 30, 1996

[54] APPARATUS FOR WIDENING A STENOSIS IN A BODY CAVITY

[75] Inventors: Wolfram Schnepp-Pesch; Josef Lindenberg, both of Karlsruhe, Germany

[73] Assignee: Angiomed AG, Karlsruhe, Germany

[21] Appl. No.: 272,046

[22] Filed: Jul. 8, 1994

Related U.S. Application Data

[63] Continuation of Ser. No. 959,616, Oct. 13, 1992, Pat. No. 5,354,309.

[30] Foreign Application Priority Data

Oct. 11, 1991 [DE] Germany ............... 91 11 733.0

[51] Int. Cl.$^6$ .................................................. A61M 29/00
[52] U.S. Cl. ........................... 606/198; 623/1; 623/11; 623/12
[58] Field of Search .......................... 606/198, 200; 623/1, 11, 12; 604/8, 96, 281

[56] References Cited

U.S. PATENT DOCUMENTS

| | | |
|---|---|---|
| 3,657,744 | 4/1972 | Ersek . |
| 3,868,956 | 3/1975 | Alfidi . |
| 4,512,338 | 4/1985 | Balko et al. . |
| 4,856,516 | 8/1989 | Hillstead . |
| 4,955,859 | 9/1990 | Zilber . |
| 5,078,736 | 1/1992 | Behl ............................................. 623/1 |
| 5,190,546 | 3/1993 | Jervis ...................................... 606/200 |
| 5,197,978 | 3/1993 | Hess ........................................... 623/1 |
| 5,344,426 | 9/1994 | Lau et al. .................................... 623/1 |
| 5,354,309 | 10/1994 | Schnepp-Pesch et al. ............. 606/198 |

FOREIGN PATENT DOCUMENTS

| | | |
|---|---|---|
| 0282175 | 9/1988 | European Pat. Off. . |
| 0380668 | 8/1990 | European Pat. Off. . |
| 2257262 | 1/1975 | France . |
| 2617721 | 7/1988 | France . |
| 9004982 | 5/1990 | WIPO . |
| WO90/04982 | 5/1990 | WIPO . |

*Primary Examiner*—Corrine M. Maglione
*Assistant Examiner*—N. Kent Gring
*Attorney, Agent, or Firm*—Antonelli, Terry, Stout & Kraus

[57] ABSTRACT

An apparatus for widening a stenosis in a body cavity, such as an artery, in the bile duct, in the ureter, etc. is proposed, which in view of a problem-free, reliable and permanent widening of a stenosis is characterized by a memory alloy part having a cylindrical jacket-shaped outer contour, said part radially widening at a transition temperature, which is above ambient temperature, but below body temperature, while maintaining a cylindrical outer contour and at a temperature below the transition temperature the diameter is smaller than that of the vessel.

12 Claims, 4 Drawing Sheets

APPARATUS FOR WIDENING A STENOSIS IN A BODY CAVITY

This is a Continuation application of U.S. Ser. No. 07/959,616, filed Oct. 13, 1992, now U.S. Pat. No. 5,354,309.

FIELD OF THE INVENTION

The invention relates to an apparatus for widening or expanding a stenosis in a body cavity, such as in an artery, in the bile duct, in the ureter, etc.

BACKGROUND ART

An occlusion in an elongated body cavity such as in a vessel, especially in an artery, is generally initially widened, in that deposition material, such as plaque is removed by cutting and sucking out or the like. However, this cannot take place up to the tissue material, because at that point an injury risk exists. If merely a narrowing and not a complete occlusion has formed, i.e. a stenosis or a certain throughflow area has been created in the aforementioned manner in the previous complete occlusion, a radial widening of the stenosis is desired. This is carried out not only in blood vessels, but also in other body passages or tubes, such as in the ureter, bile duct, etc.

For this purpose hitherto use has been made of a balloon catheter with a double internal diameter, which brings about an instantaneous radial widening, which is to remain after the catheter has been removed. Permanent widening of such a stenosis is also known. Thus, it has been proposed to axially fix a widening part to such a balloon catheter, insert it with the latter and by widening the balloon catheter to plastically deform the same in such a way that the radial dimensions of the widening part are increased, it is forced into the wall of the stenosis and after the removal of air from the catheter the latter can be removed, whereas the widening part remains in situ in the plastically deformed state. As such a part, e.g. a sleeve in the form of a "helical" envelope has been provided.

A significant disadvantage of the last-mentioned process is that the sleeve can be introduced into the stenosis located on the outer circumference of a catheter. Firstly the axial fixing is complicated and can either not be reliably achieved, so that a part can be left behind on advancing the catheter, or a subsequent release of the part from the catheter is difficult. In addition, damage can result from a widening part externally mounted on a catheter. Finally a widening by the balloon catheter in the case of such a part must lead to a radial extension, which significantly exceeds the ultimately desired radial extension, because such parts, like conventional biocompatible materials, to the extent that they have an adequate strength to keep open a stenosis, have a considerable elastic deformation range, before a permanent plastic deformation occurs to the desired radius. This more particularly applies to a "helically" shaped part of the aforementioned type.

DISCLOSURE OF THE INVENTION

The problem of the invention is therefore to provide an apparatus for widening a stenosis, which allows a simple, problem-free, reliable widening of a stenosis in a short time, while avoiding the aforementioned disadvantages.

According to the invention this problem is solved by an apparatus for widening a stenosis in a body cavity, such as in an artery, the bile duct, the ureter, etc., which is characterized by a shape memory alloy with a cylindrical jacket-like outer contour, said part radially widening, while maintaining a cylindrical contour, at a transition temperature, which is above the ambient temperature, but below the body temperature, and at a temperature below the transition temperature the diameter is smaller than that of the vessel.

The invention proposes a widening part made from a memory alloy, which assumes a shape above a certain transition temperature, which is below the body temperature, which corresponds to the desired widening of the body cavity. According to a preferred development the Emory alloy is a nickel-titanium alloy. However, it is also possible to use Cu-Zn-Al or Cu-Al-Ni alloys. Such alloys are known under the names Nitinol, Biometal (Toki, Japan), Memotal.

The martensitic reaction or transformation bringing about the shape change takes place by modifying the temperature. Whereas the transition temperature can be within wide limits, provided that it is below the body temperature, according to a preferred development the transition temperature is 20° C. This temperature is sufficiently below the temperature bringing about a reliable widening of the memory alloy part in its high temperature state. However, simultaneously the temperature is sufficiently high that a part taken by the surgeon at ambient temperature, which is therefore in its low temperature state with small radial dimensions, only radially widens after a certain time, which is adequate for inserting the part into the body up to the stenosis.

Various developments and constructions of such apparatuses are possible. Thus, the memory alloy part can comprise a bent, flat sheet metal part or can be a wire part.

In the first case, according to a preferred development the sheet metal part has a spiral shape at a temperature below the transition temperature and widens to a cylinder jacket on passing above the transition temperature. This construction has the advantage that there is no axial shortening of the widening part. The latter occurs in a preferred development, which is characterized in that the memory alloy metal is a cylinder jacket provided with elongated slots and web regions left between them, in which the parallel directed, adjacent elongated slots are reciprocally displaced in their extension direction and, accompanied by the formation of diamond-shaped gaps between the webs, the part is radially made erect on increasing the temperature to above the transition temperature. This construction can be relatively simply obtained, in that a metal sheet with the desired dimensions is punched as expanded metal, then cylindrically bent and welded together at the longitudinal edges parallel to the slots. The shortening of the part in the case of a radial widening can be taken into account from the outset by having a greater length.

The latter also applies for another preferred development, in which the part is made from a metal braid or gauze and is constructed as a cylinder jacket, or the memory alloy part is made from a multiply helically guided wire.

A particularly preferred development of the inventive apparatus is characterized in that the metallic material is constructed in meander-like manner in the axial direction and the individual meanders are bent in an almost circular manner. If the meanders have axial outward bends, then according to a preferred further development the outward bends of a meander arm are connected to an adjacent meander arm. Joining can in particular take place by soldering. If all the outward bends are not firmly joined to the adjacent meander arms in the typical manner and instead only part of them are joined, then according to another preferred development, the joining forces of the joints are greater than the "weighing" forces of the meander bends. Thus, the inventive apparatus, which can also be referred to as an endoprosthesis or stent, in the areas in which the meanders are not axially firmly joined together by joints, such as soldered joints, can be expanded or compressed and therefore position-adapted, without the joints (soldered joints) at other points fracturing or breaking.

The joining points must also be constructed as clearly defined breaking points if a stent constructed in the above-described manner is to be subsequently removed, so that on pulling at one end of the wire forming the stent the joining points break open, the wire stretches and therefore in easy manner the stent can be removed. The removal of a stent in the above-described construction, but also in a circular knitted construction or with a helically shaped stent, is facilitated if at least one end of the wire forming the apparatus a ball is provided. It is then possible to apply hollow forceps to the ball and consequently the stent can be stretched. According to another preferred construction it has a substantially axially parallel extending connecting web from which extend laterally circularly bent ribs, which extend on either side of the connecting web and are in the axial direction in each case alternately offset to one another. It is alternatively possible to provide in the case of such stents that the ribs extend under an angle of 90° to the connecting web or the ribs extend under an angle not equal to 90°, preferably an angle of 50° to 70° to the connecting web.

While the outer contour of the stents is generally cylindrical jacket-shaped, in certain individual cases conical or biconical outer contours are preferred.

According to another preferred development the metal of the thus far described catheter is embedded in tissue-compatible plastics or preferably silicone, so that despite the gaps between areas of the memory metal a closed jacket area is created. Thus, in the case of malignant tumours, it is ensured that cells do not grow into the interior of the stent.

The stent according to the invention can be used in numerous different fields and for numerous different purposes, e.g. in the urethra, ureter, neck of the bladder, deducti bilipheri, in blood vessels, such as arteries and veins, in the esophagus and trachea, as well as in the intestinal region, particularly in the intestinum rectum.

The invention offers stiff and highly flexible, particularly axially bendable stents, the latter more particularly applying for those having a wire guided in meandering manner.

BRIEF DESCRIPTION OF THE DRAWINGS

The invention is described in greater detail hereinafter relative to non-limitative embodiments and with reference to the attached drawings, wherein show.

BEST MODE FOR CARRYING OUT THE INVENTION

Figure 1A:
FIG. 1 illustrates a first embodiment of an inventive apparatus for widening a stenosis in a body cavity with the starting position in spiral form.
Figure 1B:

FIG. 1 shows a first embodiment of an inventive apparatus for widening a stenosis in an elongated body cavity,such as in an artery,the bile duct,the ureter, etc. and which is hereinafter referred to as a stent. In its low temperature state the stent of FIG. 1 has a spiral shape and which on passing above a transition temperature in its high temperature state widens to an almost cylindrical jacket-shape as illustrated to the right. The stents according to the invention are made from a shape memory metal, particularly from nickel-titanium alloys, but also Cu-Zn-Al or Cu-Al-Ni alloys. Memory alloys are known under the names Nitinol, Bimetal or Memotal. The manufacture of the stent according to FIG. 1 takes place in that in its high temperature form, i.e. the cylindrical jacket-shape of FIG. 1, the stent is bent and then undergoes a heat treatment. After cooling to below the transition temperature the stent is permanently brought into its spiral low temperature form. If it is again heated to above the transition temperature, which is in the range 30° to 35° C. and preferably at 35° C., then it "remembers" its cylindrical jacket-shaped high temperature form and reassumes the latter.

Figure 2A:
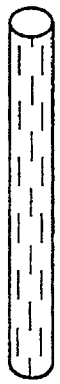
FIG. 2 illustrates another embodiment of the inventive apparatus with axially parallel slots in the form of an expanded metal.
Figure 2B:

FIG. 2 shows another stent in the form of an expanded metal. In the case of the latter into a sheet metal part are punched in successively aligned and juxtaposed manner a plurality of slots and adjacent, juxtaposed slots are in each case so reciprocately longitudinally displaced, that the two upper and lower regions of a slot overlap with the near end region of adjacent slots. Parallel elongated slots are separated by web and adjacent parallel elongated slots are displaced longitudinally. If the sheet metal is expanded transversely to the extension direction of the slots, then it can be stretched, the slots widening to diamonds as illustrated to the right. Such a sheet metal piece is bent into a cylindrical jacket shape and is interconnected, such as by welding or soldering by its longitudinal sides parallel to the slots. It is brought into its widened form showing the diamonds and as is represented to the right in FIG. 2 and is then correspondingly subject to the high temperature treatment and subsequently at low temperature is again permanently deformed in the stretched form (to the left of FIG. 2). On heating to above the transition temperature this stent also remembers its widened high temperature form. In the case of radial widening the stent of FIG. 2 and also those of FIGS. 3 and 4 shorten, unlike in the case of the stent of FIG. 1. However, this shortening can be taken into account by choosing a corresponding length. The width of the webs is extremely small and is preferably approximately 0.2 min.

Figure 3A:
FIG. 3 illustrates a further preferred embodiment based on a wire gauze.
Figure 3B:
Figure 4A:
FIG. 4 illustrates a development with a helically wound wire.
Figure 4B:
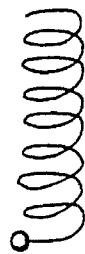

FIG. 3 shows a metal braid or gauze stent, which also has a cylindrical jacket-shaped outer contour. The temperature and shape treatment once again takes place in the above-described manner, so that on increasing the temperature to above the transition temperature the stent widens from its small diameter, stretched state into a radially widened high temperature state as illustrated to the right. The same applies with respect to the further helical design of a metal wire stent with shape memory and here again the corresponding heat treatment is carried out.

Figure 5:
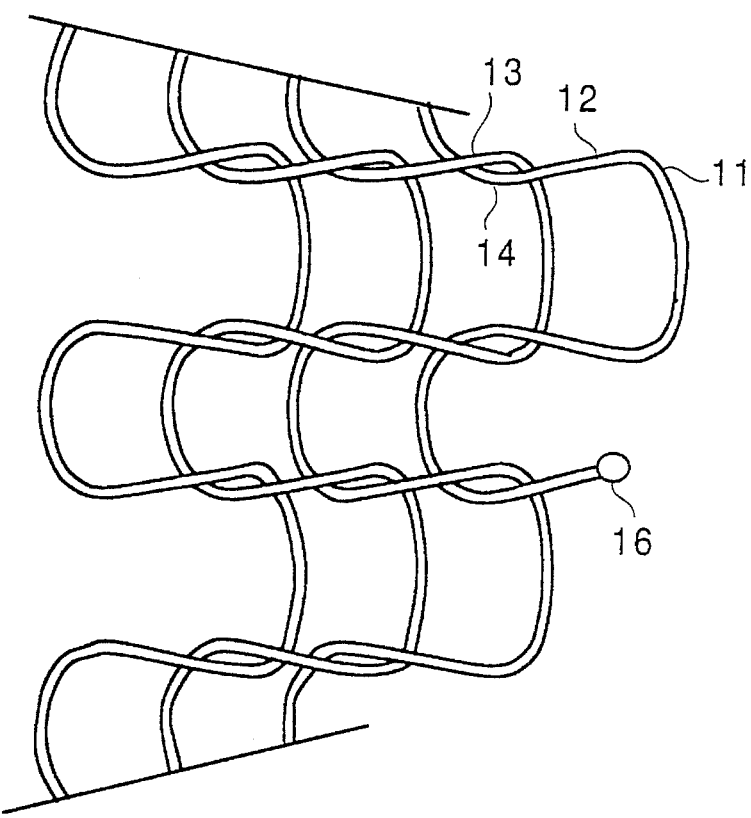
FIG. 5 illustrates the mesh pattern of a circular knitted stent according to the invention.

FIG. 5 shows the mesh pattern of an inventive, circular knitted stent. It has conventional knitted meshes formed from a weft thread 11, the meshes having a leg 12, a head 13 at the upper binding point and a base 14 at the lower binding point around which the head is placed.

According to a preferred development a ball 16 is fixed to the end of the wire filament 11. If an inserted stent is to be removed for some reason, then action can take place on the ball 16 by means of hollow forceps so as to pull the same and the mesh pattern of the stent is loosened and the latter can be removed from the body cavity in which it was positioned.

Figure 6:
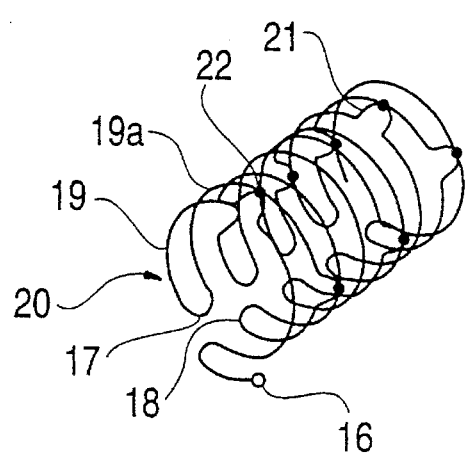
FIG. 6 illustrates a diagrammatic representation of a stent with a meandering wire, the individual meanders being bent in partial ring shape and having a cylindrical outer contour.
Figure 7:
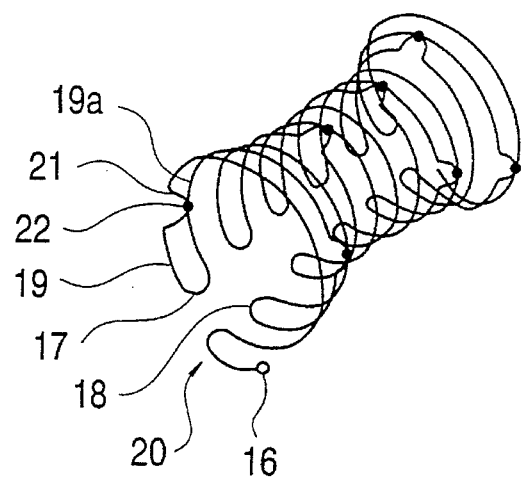
FIG. 7 illustrates a stent similar to FIG. 6 with a biconical outer contour, once again diagrammatically.

Such a removal by stretching the wire filament forming the stent is also possible in the case of the constructions according to FIGS. 6 and 7. These stents comprise a meandering, longitudinally wound wire (i.e. the meanders extend transversely to the longitudinal direction). The meanders are bent in circular manner, so that the remote webs of adjacent meanders are bent towards one another. Such a stent has the important advantage that its length can be changed without significantly influencing the cross-section. Compared with its normal longitudinal extension the stent can be compressed or stretched and is held in the resulting position by the frictional forces between it and the surrounding vessel walls.

According to a preferred development arms 19 of the meanders 20 have outward bends 21, which extend up to the adjacent meander arm, e.g. 19a. At least part of the outward bend 21 can be connected to the in each case adjacent meander arm 19a by a soldered joint 22. As a function of the intended use all the outward bends can be connected to adjacent meander arms. In this case the length of the stent is limited. Only part of the outward bends may be connected, no soldered joints being provided on certain of them and as a result the length can be changed to a limited extent. Finally, stents can be constructed in such a way that no outward bends are firmly connected to adjacent meander arms. The outward bends cause a certain resilience in the radial or angular direction of the stent.

The stents according to FIGS. 6 and 7 once again have the balls 16 at the filament ends, so as to be able to remove the stent by stretching the filament forming the same. If there are soldered joints 22, then their fastening force is much less than the tensile strength of the filament. However, it must exceed the bending force of the wire in the vicinity of the webs 17,18 of the meanders.

As in the case of other stent constructions according to the invention, the construction described above can have a cylindrical outer contour in accordance with FIG. 6. However, like other of the stents shown, it can be conical or biconical, as shown in FIG. 7 and in this case the larger diameter is on the end faces of the stent.

The inventive stent according to FIGS. 6 and 7 has very considerable flexibility, which is greater than that in the case of FIG. 5. The stent according to FIGS. 6 and 7 is almost completely bendable. The inventive metal stents can be embedded in compatible plastics or preferably silicone, which assumes the same contour as the actual stent. This makes it possible to ensure that in the vicinity of a thus designed stent a malignant tumor cannot migrate through the same.

The above-described stent formed by a meandering configuration can be used in many different ways and for many different purposes. With particular advantage such a stent can be used as a urethral stent in the vicinity of the prostate for widening the urethral area there when the prostate is enlarged. As a result of its flexibility, it adapts particularly well to the configuration of the male urethra. As a result of its longitudinal variability its length can be modified in such a way that its rear or outer end does not come to rest in the vicinity of the external sphincter, so that the stent does not impair this function. Particularly in the case of such a use the above-described stent extraction possibility by stretching the wire filament forming it and pulling out proves particularly advantageous.

Figure 8:
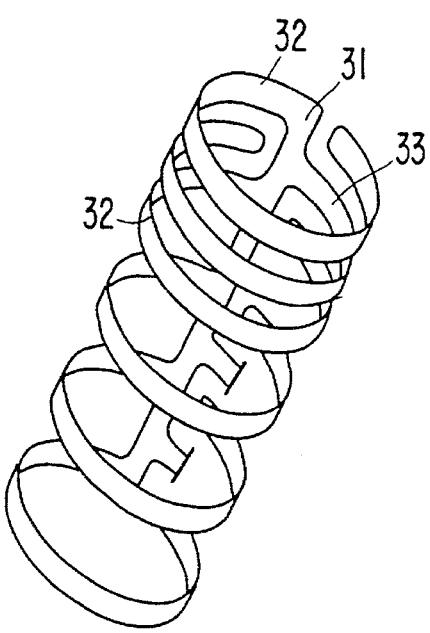
FIG. 8 illustrates another development of an inventive stent.
Figure 9:
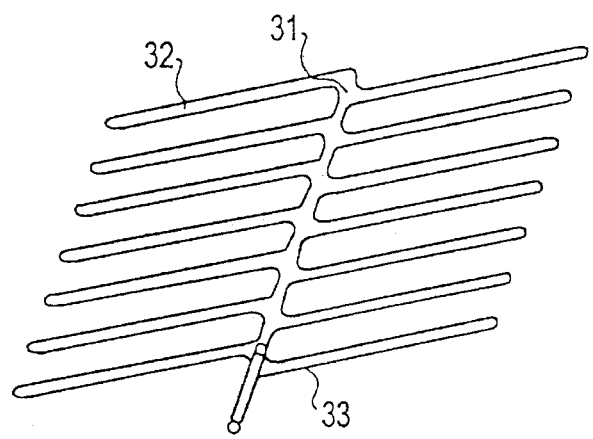
FIG. 9 illustrates a modification of the stent of FIG. 8 in the wound-on starting position.

Another preferred construction of an inventive stent is shown in FIG. 8 and FIG. 9 shows a modification in the wound-up state. Such a stent could be referred to as a "skeleton stent". It substantially has an axially parallel extending ridge, or a connecting web 31 and from it extend on either side ribs 32,33 at a right angle (FIG. 8) or under an angle differing from a right angle (FIG. 9), preferably in the range 50° to 70°. The ribs 32,33 extending to either side are in each case alternately displaced in the longitudinal direction of the ridge 31, so that the circularly bent ribs 33, which extend to one side in each case engage in the gap between two ribs, which extend to the other side and vice versa.

The length of the ribs 32,33 and the diameter of the stent in the low and high temperature position can be chosen in such a way that in the low temperature position there is an overlap of the material walls of the stent, as would otherwise be the case under identical conditions, if the ribs 32,33 extending on either side of the ridge 31 were arranged at the same height of the latter. The stent shown in FIGS. 8 and 9 also has a very considerable flexibility and longitudinal bendability. In addition, the ribs 32,33 can be so closely juxtaposed, that from the surrounding tissue of a cavity held by the stent liquid can enter and be removed from the interior of the stent. However, tissue cannot penetrate the interior and lead to a narrowing. In the construction according to FIG. 9 a somewhat greater rigidity is obtained than in the case of FIG. 8.

Figure 10:
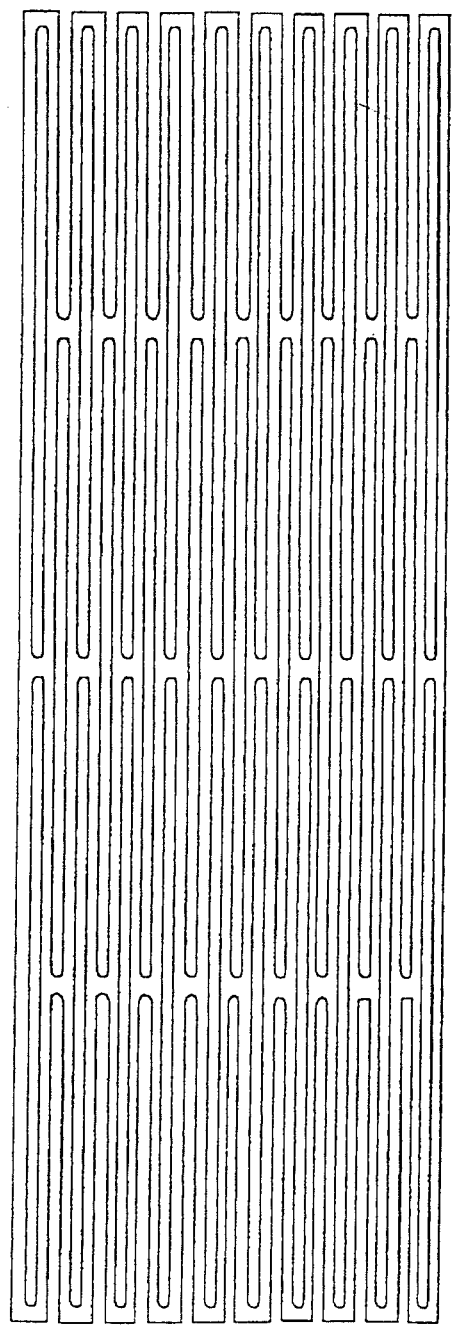
FIG. 10 illustrates the prepunched starting plate for another development of an inventive stent.

FIG. 10 shows a blank for a further stent. From a sheet metal part are punched elongated holes and juxtaposed elongated holes are alternately reciprocately displaced and can consequently give in the end regions elongated holes with a shorter length than the other elongated holes.

We claim:

1. An apparatus for widening a stenosis in a body cavity, such as in an artery, a bile duct, a ureter or the like, said apparatus comprising a memory alloy part made from a shape memory alloy and having a substantially cylindrical jacket-shaped outer contour, said memory alloy part widening radially to a radially erect contour while maintaining a cylindrical outer contour on heating said memory alloy part to above a transition temperature which is above the ambient temperature, but below the body temperature, a diameter of the cylindrical outer contour at a temperature below the transition temperature being smaller than the diameter of the body cavity, wherein said memory alloy part comprises a flat sheet metal part which is cylindrically bent to form the cylindrical jacket-shaped outer contour with the memory alloy part having, at a temperature below the transition temperature, parallel elongated slots separated by webs with adjacent parallel slots being displaced longitudinally from one another such that, on heating said memory alloy part to above the transition temperature, the cylindrically bent part is made radially erect by formation of diamond-shaped gaps between the webs by the widening of said slots.

2. An apparatus according to claim 1, wherein said memory alloy part is embedded in a closed jacket of tissue-compatible material.

3. An apparatus according to claim 2, wherein: the memory alloy is a nickel-titanium alloy.

4. An apparatus according to claim 3 wherein: the transition temperature is between 30° C. and 35° C.

5. An apparatus according to claim 4 wherein: the transition temperature is 35° C.

6. An apparatus according to claim 2 wherein: the transition temperature is between 30° C. and 35° C.

7. An apparatus according to claim 6 wherein: the transition temperature is 35° C.

8. An apparatus according to claim 1, wherein: the memory alloy is a nickel-titanium alloy.

9. An apparatus according to claim 8 wherein: the transition temperature is between 30° C. and 35° C.

10. An apparatus according to claim 9 wherein: the transition temperature is 35° C.

11. An apparatus according to claim 1 wherein: the transition temperature is between 30° C. and 35° C.

12. An apparatus according to claim 11 wherein: the transition temperature is 35° C.

* * * * *